United States Patent [19]
Riggs et al.

[11] Patent Number: 5,186,166
[45] Date of Patent: Feb. 16, 1993

[54] POWDER NEBULIZER APPARATUS AND METHOD OF NEBULIZATION

[76] Inventors: John H. Riggs, 3720 Summer Pl., Raleigh, N.C. 27604; Barry O. Mangum, 1105 Shadywood La., Raleigh, N.C. 27603

[21] Appl. No.: 846,784

[22] Filed: Mar. 4, 1992

[51] Int. Cl.⁵ ............................................. A61M 16/00
[52] U.S. Cl. ........................ 128/203.15; 128/204.25; 128/207.14; 406/93; 406/142; 137/268
[58] Field of Search .................. 128/200.14, 200.16, 128/203.12, 203.15, 203.25, 204.25, 207.14; 406/12, 29, 38, 93, 122, 134, 137, 142, 146; 222/464, 630, 635, 637, 197; 137/268

[56] References Cited

U.S. PATENT DOCUMENTS

| 1,599,959 | 9/1926 | Fujimoto | 128/203.15 |
|---|---|---|---|
| 2,693,805 | 11/1954 | Taplin | 128/203.15 |
| 2,792,971 | 5/1957 | Kaiser | 222/630 |
| 2,820,565 | 1/1959 | Martin | 222/630 X |
| 3,353,873 | 11/1967 | Dietert | 406/142 |
| 3,658,059 | 4/1972 | Steil | 128/203.15 X |
| 4,276,876 | 7/1981 | Häkkinen | 128/200.14 |
| 4,510,929 | 4/1985 | Bordoni et al. | 128/200.14 |
| 4,662,799 | 5/1987 | Paul | 406/93 X |
| 4,674,491 | 6/1987 | Brugger | 128/200.14 |
| 4,703,753 | 11/1987 | Bordoni | 128/200.14 |
| 4,758,117 | 7/1988 | Maki | 406/93 X |
| 4,823,784 | 4/1989 | Bordoni | 128/200.14 |
| 5,086,765 | 2/1992 | Levine | 128/200.21 |

FOREIGN PATENT DOCUMENTS

| 51261 | 4/1966 | Poland | 137/101.11 |
|---|---|---|---|
| 835910 | 6/1981 | U.S.S.R. | 406/142 |
| 1418218 | 8/1988 | U.S.S.R. | 406/142 |
| 2233919 | 1/1991 | United Kingdom | 128/203.12 |

OTHER PUBLICATIONS

Raabe, O. G. et al., A Signal Actuated Nebulizer for Use with Breathing Machines, Journal of Aerosol Medicine, vol. 2, No. 2, 1989, pp. 201-210.
Simonds, A. K. et al., Simple Nebuliser Modifications to Enhance Alveolar Deposition of Pentamidine, The Lancet, Oct. 21, 1989 p. 953.
Heart—High output Extended Aerosol Respiratory Therapy, product sheet of Vortran Medical Technology, Inc. Copyright 1989, 1 p.
Aerosol Therapy for Continuous Bronchodilation—Bradley Chipps, MD Updates in Cardio-Pulmonary Medicine, Nov. 16, 1989, 16 pp.
Portnoy, J. et al., Continuous terbutaline nebulization for the treatment of severe exacerbations of asthma in children, Annals of Allergy, vol. 60, Apr. 1988, pp. 368-371.
Jasper, A. C. et al., Cost-Benefit Comparison of Aerosol Bronchodilatc Delivery Methods in Hospitalized Patients, Chest, vol. 91, No. 4 Apr. 1987, pp. 614-618.
Colacone, A. et al., Continuous Nebulization of Albuterol (Salbutamo) in Acute Asthma, Chest. vol. 97, No. 3, Mar. 1990, pp. 693-697.

Primary Examiner—Edgar S. Burr
Assistant Examiner—Eric P. Raciti
Attorney, Agent, or Firm—Steven J. Hultquist

[57] ABSTRACT

A continuous flow jet nebulizing device and method for delivering respiratory powdered medication to the lungs of a patient. The nebulizer device of the present invention comprises a nebulizer housing having a lower, generally conical-shaped lower housing portion defining an interior volume enclosed by the housing, and a nozzle element at the upper portion of the housing, coaxially aligned with the cone-shaped lower portion. The nozzle element extends through the housing, with an upper inlet portion coupleable to a suitable source of compressed carrier gas, and a lower portion of the nozzle element forming a discharge structure for directing of gas downwardly to the lower extremity of the conical-shaped lower portion of the nebulizer housing. At the upper portion of the nebulizer housing is an exit port for discharge of solids-containing carrier gas from the nebulizer housing to an exterior treatment locus.

22 Claims, 3 Drawing Sheets

POWDER NEBULIZER APPARATUS AND METHOD OF NEBULIZATION

INCORPORATION BY REFERENCE OF DISCLOSURE OF COPENDING APPLICATION

The disclosure of copending U.S. patent application Ser. No. 07/729,518 filed Jul. 12, 1991 in the names of Barry O. Mangum and John H. Riggs hereby is incorporated herein by reference.

BACKGROUND OF THE INVENTION

1. Field of the Invention

The present invention relates to a powder nebulization method and a powder nebulizer apparatus used in respiratory therapy and, in particular, to a continuously connected, continuous flow powder nebulizer useful in respiratory therapy to deliver powdered medications.

2. Description of the Related Art

Critically ill patients requiring mechanical ventilation are often victims of respiratory distress syndrome, status asthmaticus and pulmonary infections. Treatment of these and other severe respiratory conditions includes medications delivered directly to the lungs of the patient.

Respiratory delivery of medication for these conditions is preferable to oral, intravenous and subcutaneous delivery because it is non-invasive, permits rapid action of medicant, requires a relatively small dosage, is not filtered through the liver of the patient, and produces a low incidence of systemic side effects.

Nebulized or aerosolized solutions are the preferred method of respiratory delivery of medication; when fragmented into small particles, medicants are more efficiently deposited near sites of medicant activity in the lung.

Respiratory medications may be delivered to the lungs of the patient as an aerosol of a liquid or a powder. Clinical aerosols are currently generated by jet or ultrasonic nebulizers, metered dose inhalers (MDI) and dry powdered inhalers.

There are two types of nebulizers for the delivery of liquid medication to the lungs: jet nebulizers and ultrasonic nebulizers. In conventional jet nebulizers, compressed gas from a compressor or hospital air line is passed through a narrow constriction know as a jet. This creates an area of low pressure, and liquid medication from a reservoir is drawn up through a feed tube and fragmented into droplets by the airstream. Only the smallest drops leave the nebulizer directly, while the majority impact on baffles and walls and are returned to the reservoir. Consequently, jet nebulization takes several minutes to complete, depending upon the initial volume.

Important disadvantages of nebulizers include low lung deposition related to the use of tidal breathing. A substantial portion of the dose used in a jet nebulizer is retained permanently as a dead or residual volume on baffles and internal walls of the nebulizer chamber and cannot be released. Generally only 2–10% of the dose placed in the nebulizer ever reaches the lung. The consequences are a higher drug dosage and longer administrative time, along with the associated cost and risk of contamination.

The second type of aerosol generator is a metered dose inhaler (MDI), which delivers a bolus of more concentrated drug aerosols than the solution commonly available for nebulizers. For optimal effect, MDI delivery systems require proper administration technique, which includes coordinated actuation of aerosol delivery with inhalation, a slow inhalation of 0.5–0.75 liters per second, a deep breath approaching inspiratory capacity inhalation, and at least 4 seconds of breath holding.

Many patients find it difficult to properly administer medication with an MDI, especially during acute exorbation. An article which appeared in *Eur. J. Respir. Dis.*, 68(5), 332 (1986), entitled "Bronchodilator Affects of a Fenoterol Meter Dose Inhaler and Fenoterol Powder in Asthmatics with Poor Inhaler Technique," described test findings showing that the effectiveness of bronchodilator medication, when delivered with an MDI, is dependent on good MDI technique. The article suggested that delivery of medication in a powdered form is more reliable for patients who do not exercise proper MDI technique.

MDI's can be equipped with devices that automatically couple actuation to inspiratory effort, thus eliminating the need for coordinating hand action with inhalation. Devices such as spacers and holding chambers also decrease partial velocity and reduce the number of large particles. Both of these features reduce oral pharyngeal and large airway deposition with a consequent reduction in systemic absorption. Deposition of aerosols from an MDI with a spacer or holding chamber is similar and perhaps better than the deposition of a properly used MDI alone.

Advantages of the MDI include deposition of 10–15% of the metered dose with consequent short treatment time, low cost and increased convenience. However, MDI's cannot be used by patients requiring mechanical ventilation. Other disadvantages include the need for patient cooperation, the practical limitations and inconveniences associated with increased dosing requirements due to the typically small dosages administered with an MDI, the limited number of currently available drugs, and the dependence on fluorocarbons for aerosol generation.

Others have recognized the need for new inhalation devices such as modified dry powder inhalers to replace use of MDI's due to environmental concerns related to the use of fluorocarbons. See "Today's Treatment of Airway Obstruction . . . and Tomorrow's?" Flenley, D. C., *Respiration,* 55 Suppl. 2, 4 (1989).

The third type of aerosol generator is a dry powdered inhaler. Dry powder inhalation devices currently in use include the inhalation devices commercially available under the trademarks "SPINHALER", "ROTAHALER", and "TURBOHALER", as well as the disc inhaler. Dry powder inhalers are breath actuated and usually require a higher inspiratory flow rate than that required for an MDI or a nebulizer. Flow rates of 1–2 liters per second are usually considered optimal, although flow rates as low as 0.5 liters per second may be effective for some dry powdered inhalers.

Advantages of dry powdered inhalers include relative ease of administration and the fact that they do not require fluorocarbon propellants. When a dry powdered inhaler is used properly, deposition appears to be similar to that of a properly used MDI.

However, powdered inhalers are limited by the dose they can provide and by the number of drugs currently available. Only terbutaline, salbutamol, dexamethasone and chromolyn sodium are available in powder form.

All conventional powder inhaler delivery systems utilize single dose capsules except the Turbuhaler for administration of terbutaline. While several devices have been developed which permit preloading of several single dose capsules, neither these devices nor the Turbuhaler have eliminated the other disadvantages of conventional powdered inhalers. See "A New Inhalation System for Bronchodilatation. Study of the Acceptance of the Ingelheim M Inhaler in Chronic Obstructive Respiratory Tract Diseases," Mutterlein, B. Schmidt, B., Fleisher, W., and Freund, E., *Fortschr. Med.*, April 15, 108(11), 225 (1990); "In Vivo Evaluation of the New Multiple Dose Powder Inhaler and the Rotahaler Using the Gama Scintigraphy," Vidaren, M., Paronen, P., Vidaren, P., Vainir, P., and Nuutinen, J., *Acta. Pharm. Nord.*, 2(1), 3 (1990); "Clinical Use of Dry Powder Systems," Crompton, G. K., *Eur. J. Respir. Dis. Suppl.*, 122, 96 (1982).

Other disadvantages of dry powdered inhalers include the following: a) they are usually not particle size-selective and thus heavy oral pharyngeal deposition may occur; b) high humidity environments may cause clumping of the particles; and c) dry powdered inhalers cannot be used in ventilatory circuits.

Currently available devices for delivery of powdered medications in respiratory therapy do not employ nebulization technology.

The use of compressed air powered jet mills as a powder generator for inhalation experiments is disclosed in "Use of a Jet Mill for Disbursing Dry Powder for Inhalation Studies," Cheng, Y. S., Marshall, T. C., Henderson, R. R., and Newton, G. J., *Am. Ind. Hya. Assoc. J.*, 46(8), 449 (1985). The jet mill consisted of an elongated channel, one material delivery jet, and two high speed air jets. Powder fed into the channel was disbursed by turbulence and centrifugal forces. The powder used in the inhalation experiments consisted of dye materials to be tested for toxicity. A flow rate of 400 liters per minute was maintained. The article does not address nebulization of powdered medication for purposes of respiratory therapy.

U.S. Pat. No. 4,232,002 discloses procedures for administering antihistamines. Methods disclosed include inhalation by a patient of mist, nebulized spray, or a cloud of fine solid particles. Products for delivery of medication include pressurized canister inhalers, portable dry powder insufflators using capsules, and nebulizers. The only dry powder delivery system described is a dry powder inhaler using capsules of dry powder in single dose units. The delivery method described involves puncturing a capsule of dry powder medication which is disbursed by means of a turbomixer to be inhaled through a mouth piece. This patent does not address continuous flow or continuous delivery of inhalable medication. It does not enablingly teach or address jet nebulization of powdered solid medications, and does not teach a nebulizer vial which connects to a nebulizer to provide a device for introducing continuous flow.

U.S. Pat. No. 3,669,113 discloses a method and device for dispensing powdered medication from a perforated container by rotating the container by pneumatic means and causing the axis of rotation of the container to precess and describe a path of precession which is contained within a generally conical surface of a precession. The mechanisms described are based on varying shaft and bearing configurations. The method of this patent is said to be especially well suited to delivery of particles less than 80 microns in diameter. The patent does not address jet nebulization, continuous flow or continuous nebulization.

Recent developments in respiration therapy involve aerosolization and delivery of nebulized liquids on a continuous basis over several hours. Such delivery stabilizes the effects of the medication over time, reduces respiratory personnel support time, and reduces the chances of respiratory circuit contamination.

In our prior co-pending U.S. patent application Ser. No. 07/729,518, filed Jul. 12, 1991, a liquid nebulizer system is disclosed comprising a nebulizer attachable nebulizer vial, a large supply vessel, and a fluid delivery system, to be used with a conventional liquid nebulizer. The liquid nebulizer system provides for continuous delivery of liquid medication from a large supply vessel into the nebulizer vial which is attached to a conventional nebulizing apparatus, permitting continuous delivery of nebulized liquid medication. The disclosure of such prior copending application is hereby incorporated herein by reference.

It would be a significant advance in the art to combine the technology of nebulization systems with the efficiency of dry powdered inhaler systems.

Accordingly, it is an object of the present invention to provide a method and apparatus for continuous respiratory delivery of nebulized powdered medication.

It is another object of the invention to provide a method and apparatus for respiratory delivery of powdered medication which may be used in ventilatory circuits.

It is another object of the invention to provide a method and apparatus which overcome the disadvantages associated with currently available respiratory medicant delivery systems.

These and other objects and advantages of the present invention will be more fully apparent from the ensuing disclosure and appended claims.

SUMMARY OF THE INVENTION

The present invention alleviates the disadvantages of conventional administration of respiratory medications. The invention provides for administration of respiratory medication with less patient coordination than that required by an MDI or dry powdered inhaler, and can be used in ventilatory circuits. No inspiratory flow rate is required of patients. A carrier flow rate as low as 0.5 to 2 liters per minute can be accommodated by the present invention, as opposed to the 6 to 8 liters per minute flow rate required by a liquid nebulizer apparatus.

The apparatus of the present invention operates without the baffling system which is used in liquid nebulization systems, thereby enabling a larger percentage of medication to be delivered to the patient instead of being retained in the apparatus. The percentage of the originally provided medication which is actually delivered to the patient by the apparatus and method of the present invention is typically greater than 20%. The size of particles produced by the invention is determined by the intrinsic physical form, e.g., molecular structure of the medicament species, not by the specific apparatus configuration and methodology of the nebulizer as in liquid nebulizer systems. Higher drug dosages can be obtained by use of the present invention than is possible with conventional respiratory medication delivery systems.

In one aspect, the present invention relates to a method of forming a solid particle dispersion in a carrier gas stream, comprising the steps of:
 (a) providing a generally conical-shaped or funicular receptacle containing particulate solid to be dispersed;
 (b) directing a jet of carrier gas downwardly toward the lower extremity of the generally conical-shaped or funicular receptacle to entrain particles of the particulate solid in the gas; and
 (c) discharging particulate solids-containing gas from the receptacle.

In a particularly preferred embodiment of the method of the present invention, the gas stream directed at the particulate solid is passed through a first nozzle, then expanded and passed through a second nozzle where an entrainment structure channels gas from the conical-shaped receptacle to the jet structure, increasing total gas flow and aiding in the production of a gas jet flow stream of desired velocity and pressure characteristics. The entrainment structure comprises a chamber defining a plenum, with an entrainment port communicating in gas flow relationship with the interior volume of the housing, and with an outlet port communicating with the second nozzle to cooperatively form a jet structure therewith.

In another aspect, the present invention relates to a continuous flow powder nebulizer medicant delivery system comprising a jet nebulizer including a conical nebulizer receptacle. The nebulizer receptacle provides a reservoir for powdered medication with a multiple dose capacity, permitting continuous delivery of medication rather than a single breath dose or periodic single doses. The present invention may be used with a ventilator circuit to deliver nebulized powdered medication and gas to patients via an endotracheal tube when necessary for critically ill patients. A mouthpiece, mask or other proximal attachment is used to deliver nebulized powdered medicant to voluntary patients.

More specifically, the nebulizer device of the present invention comprises a nebulizer housing having a generally conical-shaped or funicular lower housing portion defining an interior volume enclosed by the housing, and a gas jet member, e.g., a nozzle element, at the upper portion of the housing, generally coaxially aligned with the cone-shaped or funicular lower portion. The gas jet member extends through the housing, with an upper inlet portion coupleable to a suitable source of compressed carrier gas, and a lower portion of the gas jet member forming a nozzle or discharge structure for directing gas downwardly to the lower extremity of the conical-shaped or funicular lower portion of the nebulizer housing. At the upper portion of the nebulizer housing, in transversely outwardly spaced relationship to the gas jet member, is an exit port, for discharge of solids-containing carrier gas from the nebulizer housing to an exterior treatment locus. For example, the exit port may be suitably coupled to a ventilator or breathing circuit, comprising connecting tubing, as described hereinabove.

As used herein, the term "transverse" refers to the direction generally perpendicular to the central axis defined by the conical-shaped or funicular lower portion of the nebulizer housing.

In a particularly preferred embodiment, the above-described gas jet member is coaxially disposed in closed flow communication with a second gas jet member, with the second gas jet member having an upper portion defining a receiving volume for receiving carrier gas discharged from the nozzle or discharge end of the first gas jet member. The receiving volume is of significantly greater transverse cross-section than the discharge passage of the first gas jet member. The second gas jet member defines a lower discharge passage (nozzle portion) which is of substantially reduced transverse cross-section, relative to the receiving volume. By this arrangement, the compressed carrier gas is discharged from the first gas jet member into the receiving volume of the second gas jet member, thereby undergoing expansion, following which the gas is discharged in a high velocity jet from the nozzle portion of the second gas jet member disposed beneath the first gas jet member. Gas exiting the second gas jet member passes through an entrainment structure wherein additional gas, which is channeled from the nebulizer receptacle into the entrainment structure through an entrainment port, is entrained in the gas stream being discharged from the second gas jet member. Entrainment of gas from the nebulizer receptacle increases circulatory flow by producing a swirling effect within the nebulizer receptacle, and increases the homogeneity of the nebulized particulate-containing gas. The resultingly discharged high-velocity gas stream then engages the powdered medicament in the lower portion of the nebulizer housing, which is of progressively decreasing transverse cross-section. As a result, there is achieved a high extent of solids entrainment in the carrier gas stream, as discharged from the nebulizer housing through the exit port.

The operation of the nebulizer device of the present invention is based on a number of gas physics laws. One such principle is the Bernoulli principle, which states that where the forward velocity of a gas increases, its lateral wall pressure decreases with a corresponding increase in forward pressure. The jet structure in the nebulizer of the present invention utilizes this principle.

Use of two jets in a preferred embodiment of the nebulizer of the present invention, one above the other, forms a type of proportional amplifier, yielding greater pressure from a lower flow rate. The first jet, wherein the gas flows through a pinhole or other nozzle-forming means, causes a directed flow of carrier gas to issue from the jet. As the gas leaves this jet, the flow is allowed to expand laterally for a very small distance. The flow is then directed into a second jet comprising a nozzle-forming means, causing the flow to undergo a phenomenon described by Toricelli's law, which states that as gas flow meets a restriction, the molecules must travel faster in a forward direction than they did previously. In a preferred embodiment of the present invention, the accelerated gas flow produced according to Toricelli's law is further accelerated by entrainment of gas from the nebulizer receptacle in the gas flow by means of an entrainment structure. The principle upon which such entrainment is based is Venturi's law of air/liquid entrainment.

Simply stated, gas is directed by the nebulizer through a jet where the gas flow accelerates; in the preferred double-jet system of the invention, this accelerated gas flow then partially reexpands after exiting the jet, and flows into a second jet which further increases the pressure. The pressure of the gas being discharged from the second jet entrains gas through the entrainment structure which increases the circulatory flow of the carrier gas. In either case, the pressurized gas is directed down into the nebulizer vial with a "V"

or cone-shaped apex containing powdered medication. This creates a swirling effect in the receptacle, causing the medication to rise to the top of the nebulizer receptacle for efficient entrainment in the carrier gas and subsequent delivery to the patient.

DETAILED DESCRIPTION OF THE INVENTION, AND PREFERRED EMBODIMENTS THEREOF

The present invention provides a method and apparatus which overcome the disadvantages associated with currently available respiratory medicant delivery systems. The present invention requires less patient coordination than that required by an MDI or dry powdered inhaler, requires no inspiratory flow rate from patients, and can accommodate flow rates for the carrier gas as low as 0.5 to 2 liters per minute.

The present invention provides a method and apparatus for continuous respiratory delivery of nebulized powdered medication. In addition, the present invention provides a method and apparatus for respiratory delivery of powdered medication which may be used in ventilatory circuits. This represents an advance in the state of the art; no currently available devices for delivery of powdered medications in respiratory therapy provide for continuous delivery of nebulized powdered medication or for use with ventilatory circuits.

In this description, the term "proximal" is used to indicate the segment of the device normally closest to the patient when it is being used. The term "distal" refers to the other end. Herein the term "nebulizing device" is defined to be a nebulizing unit or instrument used to aerosolize powdered medication for delivery to a patient. The term "nebulizer receptacle" is defined to be that portion of a nebulizing device which comprises a container for a reservoir for powdered medication to be nebulized. The term "nebulizer upper portion" is defined to be the non-nebulizer-receptacle portion of the nebulizing device which comprises at least a portion of the nebulizing mechanism. Reference is now made to the embodiments illustrated in FIGS. 1–4.

Figure 1:
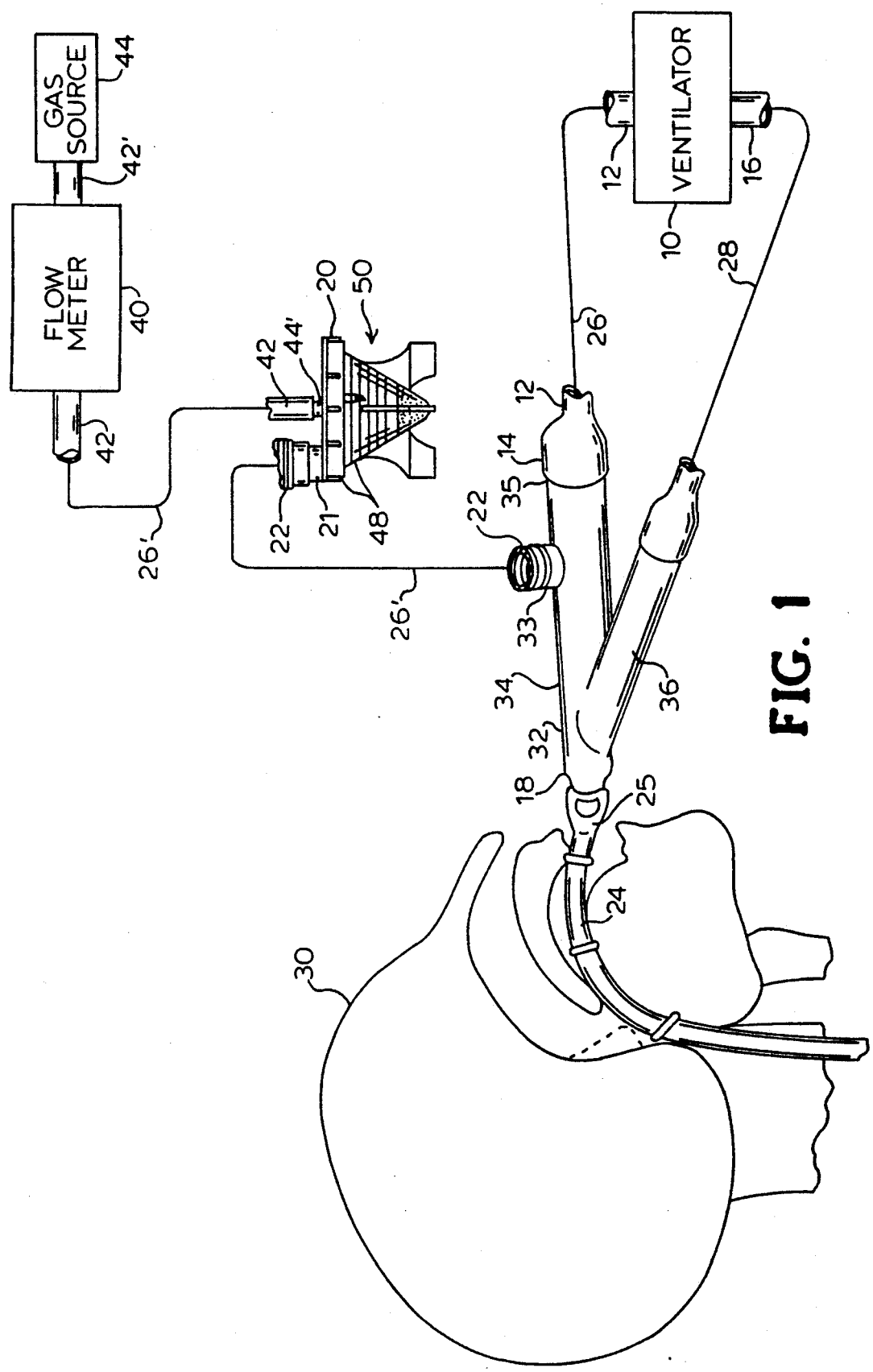
FIG. 1 is a schematic representation of a patient receiving respiratory support and continuous medication via a continuous flow nebulizing device connected to an endotracheal tube and a ventilator.

As seen in FIG. 1, a patient 30, undergoing respiratory therapy, is fitted with an endotracheal tube 24. The proximal trunk end 18 of a "Y"-shaped connector 32 is insertably connected to a distal end 25 of endotracheal tube 24. Nebulizing device 48 is connected to arm 34 of "Y"-shaped connector 32 via tube 22 which is interposed and connected between exit port 21 of nebulizer device 48 and arm 34 of the "Y"-shaped connector 32 at port 33. A distal end 35 of arm 34 is insertably connected to a proximal end 14 of gas delivery tube 12. Gas delivery tube 12 provides the distal portion of inhalation respiratory pathway 26 and connects to the output inhalation gas of a ventilator 10. Ventilator 10 thereby supplies periodic, breath-sustaining pulses of pressurized gas through tube 12 and through arm 34 of "Y"-shaped connector 32 into endotracheal tube 24 and to patient 30.

The other distal end 36 of "Y"-shaped connector 32 comprises a proximal portion of an exhalation respiratory pathway 28 which further comprises tube 16 which returns exhalation flow to ventilator 10. Many different ventilators are known and available in the art. Generally, ventilators which are currently used with nebulizers may be used with the present invention.

Nebulizer device 48 receives a supply of nebulizing gas from a flow meter 40 along a fluid pathway 26' which passes through a tube 42 interposed and connected between flow meter 40 and a top nebulizer inflow connecting tube 44'. Flow meter 40 receives a pressurized gas from a gas source 44 through a connecting tube 42'. Gas pressure from gas source 44 is sufficient to provide the volumetric flow for which flow meter 40 is preset. Gas source 44 may comprise pressurized oxygen or other breathable gas from the hospital pressurized oxygen delivery system, from a tank of compressed oxygen, a blender, directly from ventilator 10 or from other sources of pressurized gases used in respiratory therapy. Flow meters are well known and widely used in the art. Such flow meters may comprise macro and vernier adjustable controls for very accurate and precise gas flow settings. Although oxygen is preferred for some selected medicants, source 44 may supply oxygen blended with other gases.

Nebulizing device 48 comprises nebulizer upper portion 20 and a nebulizer receptacle 50. Nebulizing device 48 nebulizes or aerosolizes powdered medication contained in nebulizer receptacle 50 thereby producing a mist (particulate solids-in-gas dispersion) which is carried to patient 30 by influent flow of gas from ventilator 10 through pathway 26' and by nebulizing gas received from gas source 44.

Figure 2:
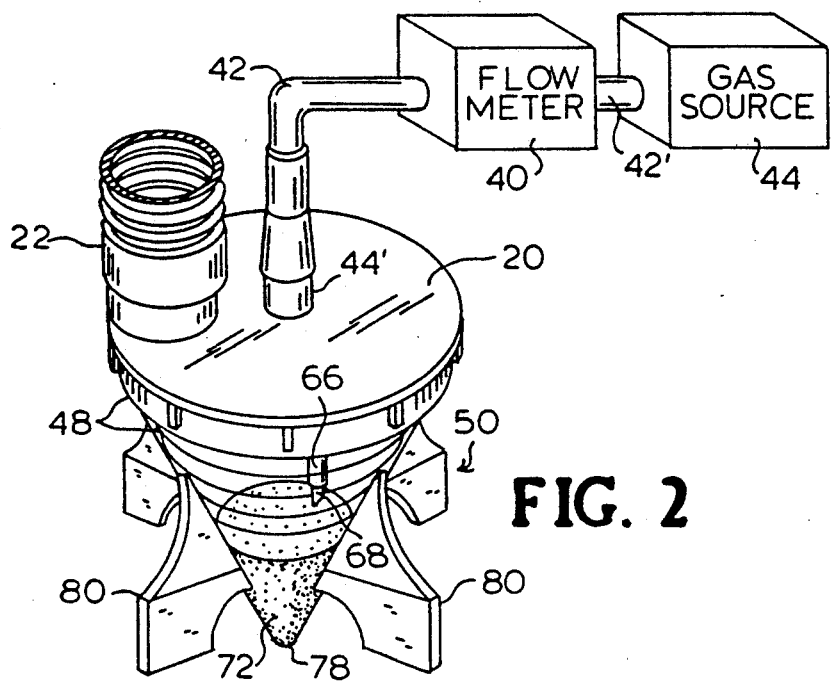
FIG. 2 is a perspective view of a nebulizer housing and supporting system comprising a nebulizer upper portion, nebulizer receptacle and influent gas flow regulating and supply devices.

As seen in FIG. 2, nebulizing device 48 comprises nebulizer receptacle 50 which is attached to nebulizer upper portion 20. In a specific embodiment, the top of the nebulizer receptacle 50 is 1.5 inches in diameter, the bottom is 0.25 inches in diameter, and the nebulizer receptacle 50 measures 1.5 inches from top to bottom. An end 68 of nozzle 66 is disposed above the surface of a reservoir 72 in the bottom of the nebulizer receptacle 50.

While specific dimensions and tolerances are illustratively set forth herein in respect of the preferred embodiments of the invention, it will be appreciated that the specific size, design, dimensions, and tolerances, may be varied widely within the broad scope of the present invention, with the choice of a specific set of such design parameters being dependent on the particular end use application contemplated in a given instance. The present invention may be embodied in the various embodiments illustrated in our prior co-pending U.S. patent application Ser. No. 07/729,518, filed Jul. 12, 1991, which is hereby incorporated herein by reference.

Figure 3:
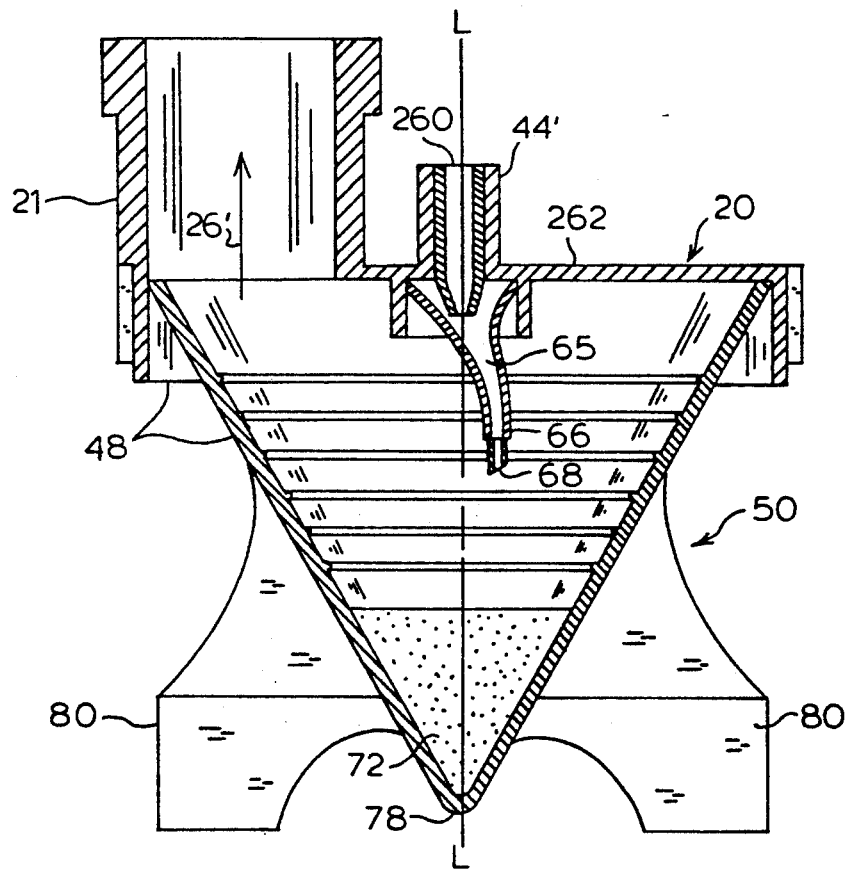
FIG. 3 is a cross section of a powder nebulizer device comprising an influent port, outlet port, and jet-producing structure.

FIG. 3 provides a sectional view of nebulizing device 48, comprising nebulizer upper portion 20 and nebulizer receptacle 50. The following description of nebulizer upper portion 20 is provided for a general understanding of the interaction between nebulizer upper portion 20 and nebulizer receptacle 50.

The nebulizer upper portion 20, as seen in FIG. 3, comprises a housing 262 which includes a nebulizer inflow connecting tube 44', a nozzle 260, and a second nozzle 66. The jet structure comprising the nozzles may, as shown, be positioned off-center relative to the centerline axis L—L of the receptacle. In the broad practice of the present invention, wherein single or multiple nozzle jet structures may be employed, the jet structure may be offset to the receptacle centerline (vertical axis) or the jet structure may be coaxial with such central axis of the receptacle, depending on the overall design, operation, and end use application of the nebulizer. Pressurized gas which provides the nebulizing high velocity gas stream for nebulization is provided through nebulizer inflow connecting tube 44'. The high velocity stream is produced by nozzle 260 and nozzle 66. The pressurized gas is discharged from the first nozzle 260 into the receiving volume 65 of the second nozzle 66, thereby undergoing expansion, following which the gas is discharged in a high velocity jet from the end 68 of nozzle 66. The resultingly discharged high-velocity gas stream then engages the powdered medication in the lower portion of nebulizer receptacle 50, which is of progressively decreasing transverse cross-section. As a result, there is achieved a high extent of solids entrainment in the gas stream, as discharged into inhalation pathway 26' via exit port 21.

While this description of the nebulizer upper portion 20 is for a single connecting tube 44', nozzle 260, nozzle 66 and associated parts, the type, number, and structure of inflow connecting tubes, nozzles, and associated nebulizer parts may vary.

Nebulizer receptacle 50 has a conical-shaped or funicular shape, is made from synthetic resinous material and is preferably transparent or at least translucent for easy monitoring of solids content by a respiratory technician or other patient attendant. Various materials of construction which are well known in the art are appropriate for the nebulizer receptacle. They are usually of chemically-inert thermoplastic such as polyolefins or polyvinyl chlorides. Their selection and fabrication are well within the skill of the art.

Apex 78 of the conical-shaped nebulizer receptacle 50 provides a containment structure for powdered medication contained in nebulizer receptacle 50. A plurality of legs 80 provide a level support when nebulizer receptacle 50 is disposed on a horizontal surface, to maintain powdered medication at the bottom of the nebulizer receptacle 50.

Figure 4:
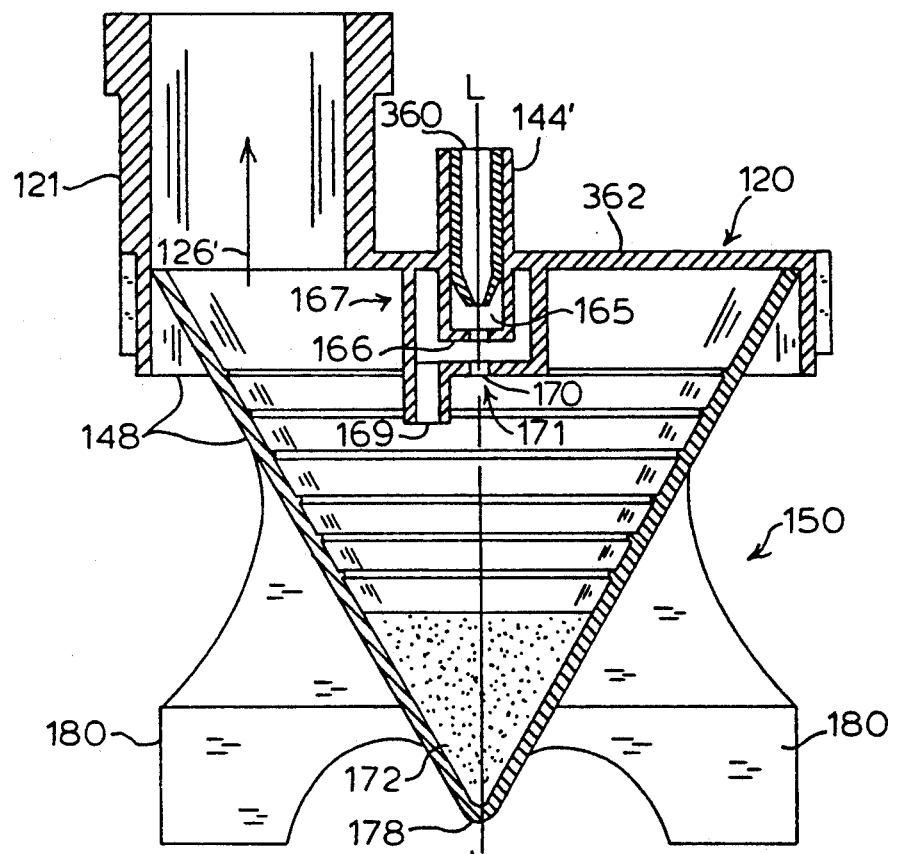
FIG. 4 is a cross section of a powder nebulizer device comprising an influent port, outlet port, jet-producing structure, and entrainment structure.

FIG. 4 provides a sectional view of nebulizing device 148, comprising nebulizer upper portion 120 and nebulizer receptacle 150. Numerals in FIG. 4 have been differentiated from numerals designating like parts in FIG. 3 by adding 100 to each such numeral.

The nebulizer upper portion 120, as seen in FIG. 4, comprises a housing 362 which includes a nebulizer inflow connecting tube 144', a first nozzle 360, and a second nozzle 166. Pressurized gas is provided through nebulizer inflow connecting tube 144'. The high velocity stream of gas for nebulization is produced by nozzle 360 and nozzle 166. The pressurized gas is discharged from the first nozzle 360 into the receiving volume 165 of the second nozzle 166, thereby undergoing expansion, following which the gas is discharged into entrainment structure 167. As the high velocity gas stream passes through entrainment structure 167, a resulting below ambient pressure within entrainment structure 167 creates a sufficient pressure differential between entrainment port 169 and nebulizer receptacle 150 to draw gas from nebulizer receptacle 150 through entrainment port 169 and into entrainment structure 167 where the entrained gas is added to the high velocity gas stream being directed toward reservoir 172. The resultingly augmented gas stream exits entrainment structure 167 through outlet port 170. The high velocity gas stream thus discharged from jet structure 171 engages the powdered medication in the lower portion of nebulizer receptacle 150, which is of progressively decreasing transverse cross-section. As a result, there is achieved a high extent of solids entrainment in the gas stream, as discharged into inhalation pathway 126' via exit port 121.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A nebulizer device for delivery of a nebulized powder material in a carrier gas to a patient, said nebulizer device comprising:
    a nebulizer housing having an upper housing portion and a generally conical-shaped or funicular lower housing portion defining an interior volume enclosed by the housing, said housing further comprising means for containing powder material to be nebulized, in the lower housing portion interior volume;
    a gas jet member at the upper portion of the housing extending through the housing, with an upper inlet portion coupleable to a source of carrier gas, and a lower portion forming a discharge structure means for directing carrier gas downwardly in a gas jet stream toward the lower extremity of the conical-shaped or funicular lower portion of the nebulizer housing for impingement on and entrainment of powder material in the lower housing portion interior volume, with the gas jet member depending downwardly from its upper inlet portion to a lower portion comprising said discharge means, and with said discharge means having a lower extremity which terminates within the upper housing portion interior volume; and
    an exit port at the upper portion of the nebulizer housing, in transversely outwardly spaced relationship to the gas jet member, for discharge of solids-containing carrier gas from the nebulizer housing to an exterior treatment locus.

2. A nebulizer device according to claim 1, further comprising a breathing circuit including a ventilator, coupled to the exit port.

3. A nebulizer device according to claim 1, further comprising means for flowing gas from a pressurized source to the gas jet member upper inlet portion to aerosolize the nebulizable powdered medication.

4. A nebulizer device according to claim 3, further comprising a pressurized gas source and a flow meter which controls the rate of gas flow to the nebulizer device thereby determining the rate of nebulization.

5. A nebulizer device according to claim 1, further comprising ventilator means, ventilator gas communicating means, and an endotracheal tube constituting a gas flow circuit, wherein the nebulizer device is interposed between the ventilator means and endotracheal tube.

6. A nebulizer device comprising:
  a nebulizer housing having a generally conical-shaped or funicular lower housing portion defining an interior volume enclosed by the housing;
  a gas jet member at an upper portion of the housing, extending through the housing, comprising a first, upper gas jet member with an upper inlet portion coupleable to a source of carrier gas, and a lower portion forming a discharge passage and a second gas jet member, with the seond gas jet member coaxially disposed in closed flow communication with the first gas jet member, with the second gas jet member having an upper portion defining a receiving volume for receiving carrier gas discharged from the discharge passage of the first gas jet member, wherein the receiving volume is of greater transverse cross-section than the discharge passage of the first gas jet member, and the second gas jet member defines a lower discharge passage, which is of substantially reduced transverse cross-section relative to the receiving volume, for directing gas downwardly to the lower extremity of the conical-shaped or funicular lower portion of the nebulizer housing; and
  an exit port at the upper portion of the nebulizer housing, in transversely outwardly spaced relationship to the gas jet member, for discharge of solids-containing carrier gas from the nebulizer housing to an exterior treatment locus.

7. A nebulizer device according to claim 1, wherein the interior volume of the conical-shaped or funicular lower portion of the nebulizer housing is devoid of any flow passage means therein.

8. A method of forming a solid particle dispersion in a carrier gas stream, for delivery to a patient, said method comprising the steps of:
  providing a nebulizer housing defining an enclosed interior volume and comprising (i) a generally conical-shaped or funicular lower housing portion containing particulate solid to be dispersed, in the lower housing portion interior volume, and (ii) an upper housing portion;
  introducing the carrier gas stream to the upper housing portion interior volume, and forming the carrier gas stream into a jet of carrier gas in said upper housing portion interior volume by passing the carrier gas stream in said upper housing portion interior volume through a first nozzle, expanding the gas from the first nozzle in an expansion zone, and passing expanded gas from the expansion zone through a second nozzle to discharge the gas in a jet, wherein the transverse cross-section of the expansion zone is substantially greater than the transverse cross-section of the first nozzle, and the transverse cross-section of the second nozzle is substantially less than the transverse cross-section of the expansion zone;
  directing the jet of carrier gas downwardly from the upper housing portion interior volume where it has been formed by gas passage through the first nozzle, expansion zone, and second nozzle, toward the lower housing portion comprising the lower extremity of the generally conical-shaped or funicular receptacle, to entrain particles of the particulate solid in the gas; and
  discharging particulate solids-containing gas from the receptacle.

9. A method according to claim 8, wherein gas is taken from the interior volume and channeled to the carrier gas being passed through the first nozzle, then expanded and passed through the second nozzle, for entrainment in said carrier gas, to produce a gas jet flow stream of selected velocity and pressure characteristics.

10. Apparatus for forming a solid particle dispersion in a carrier gas stream, said apparatus comprising:
  a generally conical-shaped or funicular receptacle means containing particulate solid to be dispensed;
  a gas jet member which directs a jet of carrier gas downwardly toward the lower extremity of the generally conical-shaped or funicular receptacle to entrain particles of the particulate solid in the gas, wherein the gas jet member comprises a first, upper gas jet member with a discharge passage and a second gas jet member disposed in closed flow communication with the first gas jet member, with the second gas jet member having an upper portion defining a receiving volume for receiving carrier gas discharged from the discharge passage of the first gas jet member, and wherein the receiving volume is of substantially greater transverse cross-section than the discharge passage of the first gas jet member, and the second gas jet member defines a lower discharge passage which is of substantially reduced transverse cross-section, relative to the receiving volume; and
  means for discharging particulate solids-containing gas from the receptacle.

11. A nebulizer device comprising:
  a nebulizer housing having a generally conical-shaped or funicular lower housing portion defining an interior volume enclosed by the housing;
  a gas jet member at the upper portion of the housing, extending through the housing, with an upper inlet portion coupleable to a source of compressed carrier gas, and a lower portion forming a discharge structure for directing gas downwardly to the lower extremity of the conical-shaped or funicular lower portion of the nebulizer housing;
  an exit port at the upper portion of the nebulizer housing, in transversely outwardly spaced relationship to the gas jet member, for discharge of solids-containing carrier gas from the nebulizer housing to an exterior treatment locus; and
  passage means for receiving gas from the interior volume and channeling same to the discharge structure for entrainment in the gas directed from the discharge structure.

12. A nebulizer device according to claim 6, further comprising passage means for receiving gas from the interior volume and channeling same to the discharge structure for entrainment in the gas directed from the discharge structure.

13. A nebulizer device according to claim 12, wherein the passage means comprise a chamber defining a plenum, with an inlet port communicating in gas flow relationship with the interior volume of the housing, and with an outlet port communicating with the second gas jet member to cooperatively form a gas discharge jet structure therewith.

14. A nebulizer device according to claim 10, further comprising means for channeling gas from the receptacle means to the gas jet member for entrainment of channeled gas in discharged particulate solids-containing gas.

15. A method according to claim 8, wherein the step of providing a jet of carrier gas comprises providing a flow rate of gas from about 0.5 to about 2 liters per minute.

16. A method according to claim 8, comprising fabricating the nebulizer housing such that the interior volume enclosed by the nebulizer housing is devoid of baffling therein.

17. A nebulizer device according to claim 1, wherein the interior volume enclosed by the nebulizer housing is devoid of baffling means therein.

18. A nebulizer device according to claim 1, wherein the gas jet member is generally co-axially aligned with the cone-shaped or funicular lower portion of the nebulizer housing.

19. A nebulizer device according to claim 1, wherein the gas jet member is positioned in the upper housing portion interior volume in off-center relationship to the central axis of the cone-shaped or funicular lower portion of the nebulizer housing.

20. A nebulizer device according to claim 1, wherein the nebulizer housing is constructed of a material of construction which is at least partially light-transmissive in character.

21. A nebulizer device according to claim 10, wherein the gas discharge passages of the first gas jet member and the second gas jet member are coaxially aligned with one another.

22. A nebulizer device according to claim 10, wherein the gas discharge passages of the first gas jet member and the second gas jet member are non-coaxial in orientation to one another.

* * * * *